United States Patent
Heidenhain (10) Patent No.: US 7,632,975 B2
(45) Date of Patent: Dec. 15, 2009

(54) PROCESS FOR THE SYNTHESIS OF ARYLFLUORENES AND ANALOGS THEREOF

(75) Inventor: Sophie Heidenhain, Lower Cambourne (GB)

(73) Assignee: CDT Oxford Limited, Cambridgeshire (GB)

( * ) Notice: Subject to any disclaimer, the term of this patent is extended or adjusted under 35 U.S.C. 154(b) by 16 days.

(21) Appl. No.: 11/722,653

(22) PCT Filed: Dec. 22, 2005

(86) PCT No.: PCT/GB2005/005032

§ 371 (c)(1),
(2), (4) Date: Mar. 6, 2008

(87) PCT Pub. No.: WO2006/067483

PCT Pub. Date: Jun. 29, 2006

(65) Prior Publication Data

US 2009/0043139 A1    Feb. 12, 2009

(30) Foreign Application Priority Data

Dec. 22, 2004    (GB)    ................... 0427965.9

(51) Int. Cl.
C07C 15/12    (2006.01)
C07D 311/78    (2006.01)
C07D 221/06    (2006.01)

(52) U.S. Cl. .................. 585/470; 549/26; 549/385; 546/101

(58) Field of Classification Search ............ 549/26, 549/385; 546/101; 585/470

See application file for complete search history.

(56) References Cited

U.S. PATENT DOCUMENTS

| 4,539,507 A | | 9/1985 | VanSlyke et al. |
| 5,101,059 A | * | 3/1992 | Carpino et al. ............. 549/388 |
| 5,302,595 A | * | 4/1994 | Cross et al. .............. 514/252.1 |
| 5,708,130 A | | 1/1998 | Woo et al. |
| 5,777,070 A | | 7/1998 | Inbasekaran et al. |
| 5,962,631 A | | 10/1999 | Woo et al. |

FOREIGN PATENT DOCUMENTS

| DE | 198 467 67 | | 4/2000 |
| EP | 1 400 578 | | 3/2004 |
| WO | WO-90/13148 | A1 | 11/1990 |
| WO | WO-95/06400 | | 3/1995 |
| WO | WO-99/21935 | | 5/1999 |
| WO | WO-99/48160 | | 9/1999 |
| WO | WO-99/54385 | | 10/1999 |
| WO | WO-00/53656 | A1 | 9/2000 |
| WO | WO-02/067343 | | 8/2002 |
| WO | WO-2004/041901 | | 5/2004 |

OTHER PUBLICATIONS

Bernius et al., "Progress with Light-Emitting Polymers," *Adv. Mater.*, 12(23):1737-1750 (2000).
Bharathan et al., "Polymer Electroluminescent Devices Processed by Inkjet Printing: I. Polymer Light-Emitting Logo," *Appl. Phys. Lett.*, 72:2660-2662 (1998).
Chang et al., "Dual-Color Polymer Light-Emitting Pixels Processed by Hybrid Inkjet Printing," *Appl. Phys. Letts.*, 73:2561-2563 (1998).
Culkin et al., "Palladium-Catalyzed α-Arylation of Carbonyl Compounds and Nitriles," *Acc. Chem. Res.*, 36:234-245 (2003).
Culkin et al., "Synthesis, Characterization, and Reactivity of Arylpalladium Cyanoalkyl Complexes: Selection of Catalysts for the α-Arylation of Nitriles," *J. Am. Chem. Soc.*, 124:9330-9331 (2002).
Grice et al., "High Brightness and Efficiency Blue Light-Emitting Polymer Diodes," *Appl. Phys. Lett.*, 73:629-631 (1998).
Hebner et al., "Ink-Jet Printing of Doped Polymers of Organic Light Emitting Devices," *Appl. Phys. Lett.*, 72:519-521 (1998).
Jorgensen et al., "Efficient Synthesis of α-Aryl Esters by Room-Temperature Palladium-Catalyzed Coupling of Aryl Halides with Ester Enolates," *J. Am. Chem. Soc.*, 124:12557-12565 (2002).
Kim et al., "Improved Operational Stability of Polyfluorene-Based Organic Light-Emitting Diodes with Plasma-Treated Indium-tin-oxide Anodes," *Appl. Phys. Lett.*, 74:3084-3086 (1999).
Lebedev et al., "Palladium (0) Complex-Catalyzed Reaction of 2-Alkenyl Acetates with CH Acids in the Presence of Bases," *Zhurnal Organicheskoi Khimii*, 22(7):1565-1566 (1986). Abstract Only.
Miyaura et al., "The Palladium-Catalyzed Cross-Coupling Reaction of Phenylboronic Acid with Haloarenes in the Presence of Bases," *Synth. Commun.*, 11:513-519 (1981).

(Continued)

Primary Examiner—Porfirio Nazario Gonzalez
(74) Attorney, Agent, or Firm—Marshall, Gerstein & Borun LLP (57) ABSTRACT

A process is provided for the synthesis of a compound of formula (I):

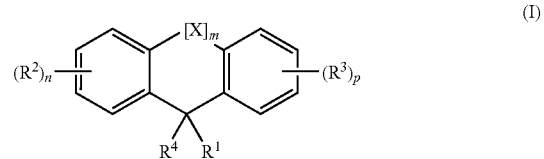

wherein:
M=0 or 1;
N and p are 0 or 1 to 4;
X is a single bond, O, S or NH;
And $R^1$-$R^4$ are as defined in claim 1.

36 Claims, 1 Drawing Sheet

OTHER PUBLICATIONS

Moradi et al., "Palladium-Catalyed α-Arylation of Esters," *J. Am. Chem. Soc.*, 123:7996-8002 (2001).

Pei et al., "Efficient Photoluminescence and Electroluminescence from a Soluble Polyfluorene," *J. Am. Chem. Soc.*, 118:7416-7417 (1996).

Service, "Self-Assembled LEDs Shine Brightly," *Science*, 279:1135 (1998).

Setayesh et al., "Polyfluorenes with Polyphenylene Dendron Side Chains: Toward Non-Aggregating, Light-Emitting Polymers," *J. Am. Chem. Soc.*, 123:946-953 (2001).

Yamamoto, "Electrically Conducting and Thermally Stable π-Conjugated Poly(arylene)s Prepared by Organometallic Process," *Prog. Polym. Sci.*, 17:1153-1205 (1992).

Combined Search and Examination Report for Application No. GB0427965.9, dated Mar. 23, 2005.

International Preliminary Report on Patentability for International Application No. PCT/GB2005/005032, dated Jun. 26, 2007.

International Search Report for International Application No. PCT/GB2005/005032, dated Apr. 24, 2006.

Written Opinion for International Application No. PCT/GB2005/005032, dated Apr. 24, 2006.

* cited by examiner

PROCESS FOR THE SYNTHESIS OF ARYLFLUORENES AND ANALOGS THEREOF

FIELD OF THE INVENTION

The invention relates to a quick, high-yield, flexible process for the synthesis of arylfluorenes and analogs thereof.

BACKGROUND OF THE INVENTION

Displays fabricated using OLEDs (organic light emitting displays) provide a number of advantages over other flat panel technologies. They are bright, colorful, fast-switching, provide a wide viewing angle, and are easy and cheap to fabricate on a variety of substrates. Organic (which here includes organometallic) LEDs may be fabricated using materials including polymers, small molecules and dendrimers, in a range of colors which depend upon the materials employed. Examples of polymer-based organic LEDs are described in WO 90/13148, WO 95/06400 and WO 99/48160; examples of dendrimer-based materials are described in WO 99/2 1935 and WO 02/067343; and examples of so called small molecule based devices are described in U.S. Pat. No. 4,539,507.

A typical OLED device comprises two layers of organic material, one of which is a layer of light emitting material such as a light emitting polymer (LEP), oligomer or a light emitting low molecular weight material, and the other of which is a layer of a hole transporting material such as a polythiophene derivative or a polyaniline derivative.

Organic LEDs may be deposited on a substrate in a matrix of pixels to form a single or multi-color pixellated display. A multi-colored display may be constructed using groups of red, green, and blue emitting pixels. So-called active matrix displays have a memory element, typically a storage capacitor and a transistor, associated with each pixel while passive matrix displays have no such memory element and instead are repetitively scanned to give the impression of a steady image. Other passive displays include segmented displays in which a plurality of segments share a common electrode and a segment may be lit up by applying a voltage to its other electrode. A simple segmented display need not be scanned but in a display comprising a plurality of segmented regions the electrodes may be multiplexed (to reduce their number) and then scanned.

Figure 1A:
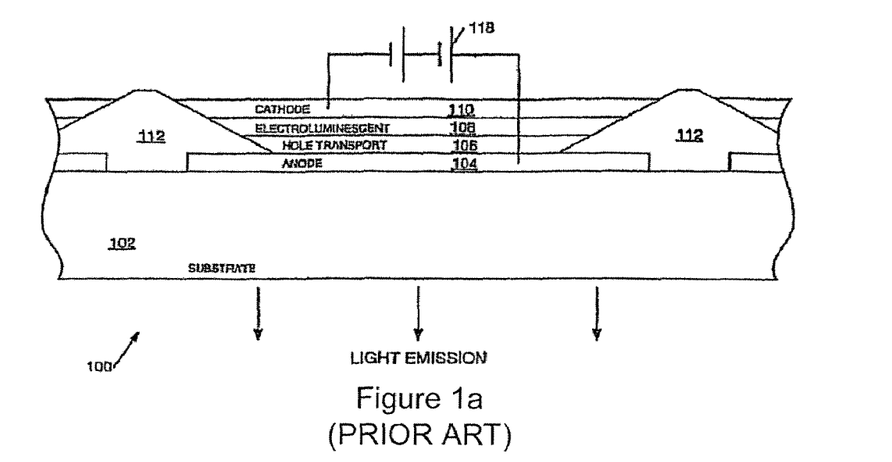
FIG. 1a shows a vertical cross-section view through an OLED device of the prior art.

FIG. 1a shows a vertical cross section through an example of an OLED device 100. In an active matrix display part of the area of a pixel is occupied by associated drive circuitry (not shown in FIG. 1a). The structure of the device is somewhat simplified for the purposes of illustration.

The OLED 100 comprises a substrate 102, typically 0.7 mm or 1.1 mm glass but optionally clear plastic or some other substantially transparent material. An anode layer 104 is deposited on the substrate, typically comprising around 150 nm thickness of ITO (indium tin oxide), over part of which is provided a metal contact layer. Typically the contact layer comprises around 500 nm of aluminum, or a layer of aluminum sandwiched between layers of chrome, and this is sometimes referred to as anode metal. Glass substrates coated with ITO and contact metal are available from Corning, USA. The contact metal over the ITO helps provide reduced resistance pathways where the anode connections do not need to be transparent, in particular for external contacts to the device. The contact metal is removed from the ITO where it is not wanted, in particular where it would otherwise obscure the display, by a standard process of photolithography followed by etching.

A substantially transparent hole transport layer 106 is deposited over the anode layer, followed by an electroluminescent layer 108, and a cathode 110. The electroluminescent layer 108 may comprise, for example, a PPV (poly(p-phenylenevinylene)) and the hole transport layer 106, which helps match the hole energy levels of the anode layer 104 and electroluminescent layer 108, may comprise a conductive transparent polymer, for example PEDOT:PSS (polystyrene-sulphonate-doped polyethylene-dioxythiophene) from Bayer AG of Germany. In a typical polymer-based device the hole transport layer 106 may comprise around 200 nm of PEDOT; a light emitting polymer layer 108 is typically around 70 nm in thickness.

These organic layers may be deposited by spin coating (afterwards removing material from unwanted areas by plasma etching or laser ablation) or by inkjet printing. In this latter case banks 112 may be formed on the substrate, for example using photoresist, to define wells into which the organic layers may be deposited. Such wells define light emitting areas or pixels of the display.

The cathode layer 110 typically comprises a low work function metal such as calcium or barium (for example deposited by physical vapor deposition) covered with a thicker, capping layer of aluminum. Optionally an additional layer may be provided immediately adjacent the electroluminescent layer, such as a layer of lithium fluoride, for improved electron energy level matching. Mutual electrical isolation of cathode lines may achieved or enhanced through the use of cathode separators (not shown in FIG. 1a).

The same basic structure may also be employed for small molecule devices.

Typically a number of displays are fabricated on a single substrate and at the end of the fabrication process the substrate is scribed, and the displays separated before an encapsulating can is attached to each to inhibit oxidation and moisture ingress.

To illuminate the OLED power is applied between the anode and cathode, represented in FIG. 1a by battery 118. In the example shown in FIG. 1a light is emitted through the transparent anode 104 and the substrate 102 and the cathode is generally reflective; such devices are referred to as "bottom emitters." Devices which emit through the cathode ("top emitters") may also be constructed, for example by keeping the thickness of cathode layer 110 less than around 50-100 nm so that the cathode is substantially transparent.

Organic LEDs may be deposited on a substrate in a matrix of pixels to form a single or multi-color pixellated display. A multicolored display may be constructed using groups of red, green, and blue emitting pixels. In such displays the individual elements are generally addressed by activating row (or column) lines to select the pixels, and rows (or columns) of pixels are written to, to create a display. So-called active matrix displays have a memory element, typically a storage capacitor and a transistor, associated with each pixel while passive matrix displays have no such memory element and instead are repetitively scanned, somewhat similarly to a TV picture, to give the impression of a steady image.

Figure 1B:
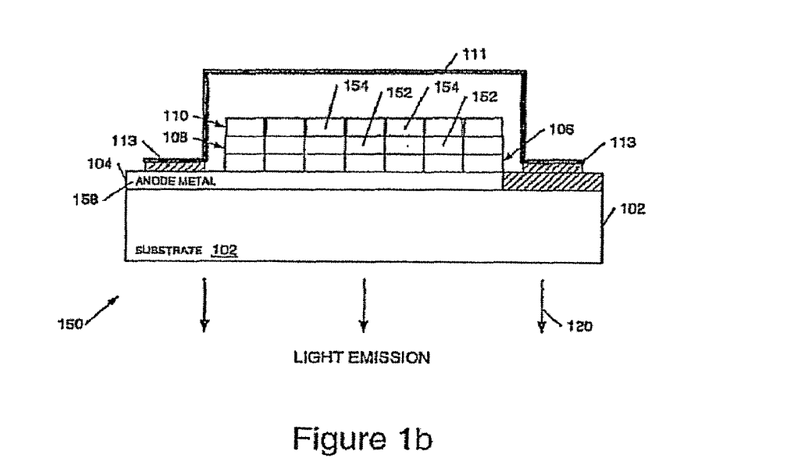
FIG. 1b shows a simplified vertical cross-sectional view through a passive matrix OLED display device.

Referring now to FIG. 1b, this shows a simplified cross-section through a passive matrix OLED display device 150, in which like elements to those of FIG. 1a are indicated by like reference numerals. As shown the hole transport 106 and electroluminescent 108 layers are subdivided into a plurality of pixels 152 at the intersection of mutually perpendicular anode and cathode lines defined in the anode metal 104 and cathode layer 110 respectively. In the figure conductive lines 154 defined in the cathode layer 110 run into the page and a cross-section through one of a plurality of anode lines 158 running at right angles to the cathode lines is shown. An electroluminescent pixel 152 at the intersection of a cathode and anode line may be addressed by applying a voltage between the relevant lines. The anode metal layer 104 provides external contacts to the display 150 and may be used for both anode and cathode connections to the OLEDs (by running the cathode layer pattern over anode metal lead-outs).

The above mentioned OLED materials, and in particular the light emitting polymer material and the cathode, are susceptible to oxidation and to moisture. The device is therefore encapsulated in a metal can 111, attached by UV-curable epoxy glue 113 onto the anode metal layer 104, small glass beads within the glue preventing the metal can touching and shorting out the contacts. Preferably the anode metal contacts are thinned where they pass under the lip of the metal can 111 to facilitate exposure of glue 113 to UV light for curing.

Considerable effort has been dedicated to the realization of a full-color, all plastic screen. The major challenges to achieving this goal have been: (1) access to conjugated polymers emitting light of the three basic colors red, green and blue; and (2) the conjugated polymers must be easy to process and fabricate into full-color display structures. PLED devices show great promise in meeting the first requirement, since manipulation of the emission color can be achieved by changing the chemical structure of the conjugated polymers. However, while modulation of the chemical nature of conjugated polymers is often easy and inexpensive on the lab scale it can be an expensive and complicated process on the industrial scale. The second requirement of the easy processability and build-up of full-color matrix devices raises the question of how to micro-pattern fine multicolor pixels and how to achieve full-color emission. Inkjet printing and hybrid inkjet printing technology have attracted much interest for the patterning of PLED devices (see, for example, R. F. Service, *Science* 1998, 279, 1135; Wudl et al., *Appl. Phys. Lett.* 1998, 73, 2561; J. Bharathan, Y. Yang, *Appl. Phys. Lett.* 1998, 72, 2660; and T. R. Hebner, C. C. Wu, D. Marcy, M. L. Lu, J. Sturm, *Appl. Phys. Lett.* 1998, 72, 519).

In order to contribute to the development of a full-color display, conjugated polymers exhibiting direct color-tuning, good processability and the potential for inexpensive large-scale fabrication have been sought. The step-ladder polymer poly-2,7-fluorenes have been the subject of much research into blue-light emitting polymers (see, for example, A. W. Grice, D. D. C. Bradley, M. T. Bernius, M. Inbasekaran, W. W. Wu, and E. P. Woo, Appl. Phys. Lett. 1998, 73, 629; J. S. Kim, R. H. Friend, and F. Cacialli, Appl. Phys. Lett. 1999, 74, 3084; WO-A-00/55927 and M. Bernius et al., Adv. Mater., 2000, 12, No. 23, 1737). This class of conjugated polymers possesses excellent processability, endowed by the attachment of solubilizing groups (particularly aryl groups) at the remote C-9 position, without hampering the extended conjugation and therefore leading to high fluorescence quantum yields in the solid state (see, for example, Q. Pei, Y. Yang, J. Am. Chem. Soc. 1996, 118, 7416). Other benefits of poly-9,9-diaryl-substituted fluorenes are their excellent thermal (Td>400° C.) and chemical stability and their good film forming properties.

The process to make homo- and copolymers based on 9,9-disubstituted fluorene monomers depends on the metal-mediated cross coupling of both AA-BB and AB type monomers. There is now a considerable prior art in the field. Such copolymers may be made by the cross coupling of dibromo-substituted monomers by contacting them with a Ni(0) catalyst formed in situ from a Ni(II) salt (the Yamamoto coupling, *Progress in Polymer Science*, Vol. 17, p. 1153, 1992) (E. P. Woo et al., U.S. Pat. Nos. 5,708,130; 5,962,631). A Pd(0) mediated cross coupling between arylboronic acids and esters and aryl or vinyl halides (the Suzuki coupling, A. Suzuki et al., *Synth. Commun.*, 1981, 11, 513) has been developed in the presence of a phase transfer catalyst and an inorganic base to make relatively high quality poly(fluorene) derivatives for applications as PLEDs (M. Inbasekaran, U.S. Pat. No. 5,777, 070). Extension to various comonomers having hole transporting properties has also been realised (WO-A-99/54385). In a further development a combination of a catalyst and a base was selected to convert the boron functional groups into —BX$_3$— where X is either F or OH (WO-A-00/53656).

One problem associated with the synthesis of these homo- and copolymers is the fact that the corresponding 2,7-derivatized monomers such as 2,7-dibromo-substituted 9,9-diarylfluorenes are difficult to synthesize. There are a number of methods currently used, none of which are very satisfactory due to their relatively poor yields and difficulties in scaling up the processes. For example, one of the most commonly used methods currently employed for the synthesis of 2,7-dibromo-9,9-diphenylfluorene is the following 5-step process disclosed in DL 198 467 67:

The yield of only 40% over 5 steps is poor and the technique itself lacks flexibility to allow different types of functionality to be introduced at the 9-position. It is highly desirable to develop a quicker, more flexible process that would enable diarylfluorene monomers and analogs thereof to be synthesized in fewer steps at a higher yield, said process being one that can readily be applied at an industrial scale.

GENERAL DESCRIPTION OF THE INVENTION

In a first aspect of the invention there is provided a process for the synthesis of a compound of formula (I):

(I)

wherein:
m=0 or 1;
n and p are the same or different and each is 0 or an integer from 1 to 4;
X is a single bond, O, S or NH;
$R^1$ is selected from the group consisting of hydrogen atoms, alkyl groups as defined below, alkenyl groups as defined below, alkynyl groups as defined below, aryl groups as defined below and heteroaryl groups as defined below;
$R^4$ is selected from the group consisting of aryl groups as defined below and heteroaryl groups as defined below; and
each $R^2$ and $R^3$ is the same or different and is selected from the group consisting of alkyl groups as defined below, alkenyl groups as defined below, alkynyl groups as defined below, haloalkyl groups as defined below, cyano groups, nitro groups, halogen atoms, hydroxyl groups, carboxy groups, alkoxycarbonyl groups as defined below, alkylcarbonyl groups as defined below, alkoxy groups as defined below, haloalkoxy groups as defined below, alkoxyalkyl groups as defined below, aryl groups as defined below, heteroaryl groups as defined below, aryloxy groups as defined below and aralkyl groups as defined below, or
two $R^2$ groups on adjacent carbon atoms together represent a group of formula (II):

(II)

wherein:
q is 0 or an integer from 1 to 4;
Y is a single bond, $CH_2$, O, S or NH;
$R^8$ is selected from the group consisting of alkyl groups as defined below, alkenyl groups as defined below, alkynyl groups as defined below, aryl groups as defined below and heteroaryl groups as defined below; and
each $R^5$ is the same or different and is selected from the group consisting of alkyl groups as defined below, alkenyl groups as defined below, alkynyl groups as defined below, haloalkyl groups as defined below, cyano groups, nitro groups, halogen atoms, hydroxyl groups, carboxy groups, alkoxycarbonyl groups as defined below, alkylcarbonyl groups as defined below, alkoxy groups as defined below, haloalkoxy groups as defined below, alkoxyalkyl groups as defined below, aryl groups as defined below, heteroaryl groups as defined below, aryloxy groups as defined below and aralkyl groups as defined below, and/or
two $R^3$ groups on adjacent carbon atoms together represent a group of formula (III):

(III)

wherein:
r is 0 or an integer from 1 to 4;
Z is a single bond, $CH_2$, O, S or NH;
$R^6$ is selected from the group consisting of alkyl groups as defined below, alkenyl groups as defined below, alkynyl groups as defined below, aryl groups as defined below and heteroaryl groups as defined below; and
each $R^7$ is the same or different and is selected from the group consisting of alkyl groups as defined below, alkenyl groups as defined below, alkynyl groups as defined below, haloalkyl groups as defined below, cyano groups, nitro group halogen atoms, hydroxyl groups, carboxy groups, alkoxycarbonyl groups as defined below, alkylcarbonyl groups as defined below, alkoxy groups as defined below, haloalkoxy groups as defined below, alkoxyalkyl groups as defined below, aryl groups as defined below, heteroaryl groups as defined below, aryloxy groups as defined below and aralkyl groups as defined below;

said alkyl groups are straight or branched alkyl groups having from 1 to 20 carbon atoms;
said alkenyl groups are straight or branched alkenyl groups having from 2 to 20 carbon atoms;
said alkynyl groups are straight or branched alkynyl groups having from 2 to 20 carbon atoms;
said aryl groups are aromatic hydrocarbon groups having from 6 to 14 carbon atoms in one or more rings which may optionally be substituted with at least one substituent selected from the group consisting of cyano groups, nitro groups, halogen atoms, hydroxyl groups, carboxy groups, alkoxycarbonyl groups as defined below, alkylcarbonyl groups as defined below, amino groups, alkoxy groups as defined below, alkyl groups as defined above, haloalkyl groups as defined below, alkoxyalkyl groups as defined below, aryl groups, aryloxy groups as defined below and aralkyl groups as defined below;
said heteroaryl groups are 5- to 7-membered aromatic heterocyclic groups containing from 1 to 3 heteroatoms selected from the group consisting of sulfur atoms, oxygen atoms and nitrogen atoms, said groups optionally being substituted with at least one substituent selected from the group consisting of cyano groups, nitro groups, halogen atoms, hydroxyl groups, carboxy groups, alkoxycarbonyl groups as defined below, alkylcarbonyl groups as defined below, amino groups, alkoxy groups as defined below, alkyl groups as defined above, haloalkyl groups as defined below, alkoxyalkyl groups as defined below, aryl groups as defined above, aryloxy groups as defined below and aralkyl groups as defined below;
said haloalkyl groups are alkyl groups as defined above which are substituted with at least one halogen atom;

said alkoxy groups are alkyl groups as defined above that are bonded to an oxygen atom;

said haloalkoxy groups are alkoxy groups as defined above that are substituted with at least one halogen atom;

said aryloxy groups are aryl groups as defined above that are bonded to an oxygen atom;

said alkoxyalkyl groups are alkyl groups as defined above that are substituted with at least one alkoxy group as defined above;

said alkylcarbonyl groups are carbonyl groups substituted with a hydrogen atom or an alkyl group as defined above;

said alkoxycarbonyl groups are carbonyl groups substituted with an alkoxy group as defined above; and said aralkyl groups are alkyl groups as defined above that are substituted by at least one aryl group as defined above;

said process comprising reacting a compound of formula (IV):

wherein $R^1$, $R^2$, $R^3$, X, m, n and p are as defined above, with a compound of formula $R^4$—L, wherein $R^4$ is as defined above and L is a leaving group, in the presence of a palladium catalyst and a base.

DETAILED DESCRIPTION

As previously indicated, palladium catalyzed coupling reactions are known in the art, but not for the synthesis of diaryl fluoroenes and analogs thereof. Examples of such Pd catalyzed reactions include Suzuki coupling, Stille coupling, and Buchwald coupling:

It will be readily apparent that these palladium catalyzed reactions differ significantly from the process of the invention, which involves the coupling of a compound of the type $Ar^1$—L wherein L is a leaving group such as a halide or a tosylate with a compound having an acidic C—H group in the presence of a palladium catalyst and a base (to deprotonate the C—H group). Reactions that involve substitution of an acidic hydrogen by an aryl carbocation have previously been disclosed for the α-arylation of ketones and enolates [see, for example, D A Culkin & J F Hartwig, *Accounts of Chemical Research* (2003), 36(4), 234-245] and of benzylic C—H positions [see, for example, J F Hartwig et al, *J Am Chem Soc* 2002, 124, 12557-12565; J F Hartwig & D A Culkin, *J Am Chem Soc* 2002, 124, 9330-9331; and W A Moradi & S L Buchwald, *J Am Chem Soc* 2001, 123, 7996-8002]. However, it has never previously been disclosed or suggested that a benzylic carbanion could be generated at the C-9 position of a fluorene-type compound (by deprotonation with a base) and reacted with a palladium inserted aryl halide or similar leaving group (Ar—Pd—L).

Taking the diphenylation of fluorene at the 9-position as an example, the deprotonated C-9 carbon atom of the fluorene group and the palladium inserted phenyl halide or similar leaving group are reacted, as illustrated below:

Having synthesized the diphenylated compound, this can then be readily derivatized if desired, e.g. at the 2- and 7-positions of the fluorene moiety to introduce leaving groups such as bromine atoms to give the final target 2,7-derivatized monomer:

Taking this as an example, the yield for the first step (from the cheap and readily available starting material fluorene) is in excess of 80%, and the second step (which is a straightforward halogenation) also provides good yields. Thus, adoption of the palladium catalyzed arylation as the first step enables 2,7-dibromo-9,9-diphenylfluorene to be produced in a simple, two-step process at an overall yield of 73%. This, is considerably quicker and gives a much higher yield than the five-step process disclosed in DE 198 467 67 which has an overall yield of only 40%.

The palladium catalyst may be any suitable for a reaction that involves the substitution of an acidic hydrogen by an aryl carbocation [e.g. those disclosed in D A Culkin & J F Hartwig, *Accounts of Chemical Research* (2003), 36(4), 234-245; J F Hartwig et al, *J Am Chem Soc* 2002, 124, 12557-

12565; J F Hartwig & D A Culkin, *J Am Chem Soc* 2002, 124, 9330-9331; and W A Moradi & S L Buchwald, *J Am Chem Soc* 2001, 123, 7996-8002]. The palladium catalyst can be in the form of Pd(0) or Pd(II), e.g. palladium (II) acetate or bis(dibenzenylidenacetone) palladium (0) (Pd$_2$dba$_3$).

Preferably, the palladium catalyst should comprise a phosphine ligand, either by:

(i) mixing a palladium catalyst such as palladium (II) acetate or bis(dibenzenylidenacetone) palladium (0) or PdCl$_2$ (o-tol)$_2$ with a phosphine, preferred examples of which include trialkylphosphines (wherein each alkyl group is the same or different and is as defined above, preferably methyl, ethyl or t-butyl), tricycloalkylphosphines (wherein each cycloalkyl group is the same or different and has from 3 to 7 carbon atoms, preferably cyclopropyl, cyclobutyl, cyclopentyl or cyclohexyl) and triarylphosphines (wherein each aryl group is the same or different and is an aromatic hydrocarbon group having from 6 to 14 carbon atoms in one or more rings which may optionally be substituted with at least one substituent selected from the group consisting of cyano groups, nitro groups, halogen atoms, hydroxyl groups, carboxy groups, alkoxycarbonyl groups as defined above, alkylcarbonyl groups as defined above, amino groups optionally substituted by one or two alkyl groups as defined above, alkoxy groups as defined above, alkyl groups as defined above, haloalkyl groups as defined above, alkoxyalkyl groups as defined above, aryl groups, aryloxy groups as defined above and aralkyl groups as defined above, preferably phenyl and naphthyl); particularly preferred examples of such phosphines include triphenylphosphine, tri(t-butyl)phosphine, tricyclohexylphosphine, (ii) including the phosphine group as a ligand of the palladium complex, e.g. PdCl$_2$(PPh3)$_2$ or tetrakis(triphenylphosphine)palladium (0).

Of these alternatives, a mixture of a palladium (0) or palladium (II) catalyst, [preferably palladium (II) acetate or bis(dibenzenylidenacetone) palladium (0)], with a phospine selected from the group consisting of tricyclohexylphosphine, triphenylphosphine and tributylphospine, and the phosphine-containing palladium catalyst PdCl$_2$(PPh$_3$)$_2$ are more preferred and a mixture of bis(dibenzenylidenacetone) palladium (0) or palladium (II) acetate with tricylcohexylphosphine is most preferred. In the mixtures, the molar ratio of palladium to phosphine compound is any suitable to catalyze the desired reaction, and may typically be in the range of from 10:1 to 1:10, more typically 5:1 to 1:5, yet more typically 2:1 to 1:2, e.g. 1:1.

The amount of palladium catalyst used can vary quite significantly, as long as the amount present is sufficient to catalyze the desired aryl insertion reaction. Typically, the number of molar equivalents of palladium catalyst used compared to the amount of starting compound of formula (IV) is from 0.1 to 10%; more typically it is from 0.2 to 5%; yet more typically it is from 0.5 to 2%; and preferably it is from 0.5-1%.

In one preferred embodiment, the substituent R$^1$ in the compound of formula (IV) is a hydrogen atom and 2 or more molar equivalents of the compound of formula R$^4$—L are used compared to the amount of the compound of formula (IV), the result being substitution of 2 aryl or heteroaryl groups of formula R$^4$ at the acidic proton position, i.e. the reaction is as follows:

Where substituents R$^1$, R$^2$, R$^3$, R$^5$, R$^6$, R$^7$ or R$^8$ are alkyl substituents, said alkyl groups are straight or branched alkyl groups having from 1 to 20 carbon atoms and each may be the same or different. Each may be, for example, a methyl, ethyl, propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group. Preferred examples include methyl, ethyl, isopropyl and t-butyl groups.

Where substituents R$^1$, R$^2$, R$^3$, R$^5$, R$^6$, R$^7$ or R$^8$ are alkenyl groups, said alkenyl groups are straight or branched alkenyl groups having from 2 to 20 carbon atoms and each may be the same or different. Each may be, for example, a vinyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4- pentenyl, 2-methyl-4-pentenyl, 2-hexenyl, 3-hexenyl, 4-hexenyl or 5-hexenyl group. Preferred examples include vinyl and 2-propenyl groups.

Where substituents $R^1$, $R^2$, $R^3$, $R^5$, $R^6$, $R^7$ or $R^8$ are alkynyl groups, said alkynyl groups are straight or branched alkynyl groups having from 2 to 20 carbon atoms and each may be the same or different. Each may be, for example, an ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl group. Preferred examples include ethynyl and 2-propynyl groups.

Where substituents $R^1$, $R^2$, $R^3$, $R^5$, $R^6$, $R^7$ or $R^8$ are aryl groups, said aryl groups are aromatic hydrocarbon groups having from 6 to 14 carbon atoms in one or more rings which may optionally be substituted with at least one substituent selected from the group consisting of cyano groups, nitro groups, halogen atoms, hydroxyl groups, carboxy groups, alkoxycarbonyl groups as defined above, alkylcarbonyl groups as defined above, amino groups, alkoxy groups as defined above, alkyl groups as defined above, haloalkyl groups as defined above, alkoxyalkyl groups as defined above, aryl groups, aryloxy groups as defined above and aralkyl groups as defined above and each may be the same or different. Each may be, for example, a phenyl, naphthyl, phenanthryl or anthracenyl group. Preferred examples include phenyl and naphthyl groups.

Where substituents $R^1$, $R^2$, $R^3$, $R^5$, $R^6$, $R^7$ or $R^8$ are heteroaryl groups, said heteroaryl groups are 5- to 7-membered aromatic heterocyclic groups containing from 1 to 3 heteroatoms selected from the group consisting of sulfur atoms, oxygen atoms and nitrogen atoms, said groups optionally being substituted with at least one substituent selected from the group consisting of cyano groups, nitro groups, halogen atoms, hydroxyl groups, carboxy groups, alkoxycarbonyl groups as defined above, alkylcarbonyl groups as defined above, amino groups, alkoxy groups as defined above, alkyl groups as defined above, haloalkyl groups as defined above, alkoxyalkyl groups as defined above, aryl groups as defined above, aryloxy groups as defined above and aralkyl groups as defined above and each may be the same or different. Each may be, for example, a furyl, thienyl, pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl or pyrazinyl group. Preferred examples include furyl, thienyl, pyrrolyl and pyridyl groups.

Where substituents $R^1$, $R^2$, $R^3$, $R^5$, $R^6$, $R^7$ or $R^8$ are haloalkyl groups, said haloalkyl groups are alkyl groups as defined above which are substituted with at least one halogen atom and each may be the same or different. Each may be, for example, a trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl or 2,2-dibromoethyl group. Preferred examples include trifluoromethyl, difluoromethyl, dichloromethyl, 2-fluoroethyl and 2,2,2-trifluoroethyl groups.

Where substituents $R^1$, $R^2$, $R^3$, $R^5$, $R^6$, $R^7$ or $R^8$ are alkoxy groups, said alkoxy groups are alkyl groups as defined above that are bonded to an oxygen atom and each may be the same or different. Each may be, for example, an alkoxy group having 1 to 4 carbon atoms, such as a methoxy, ethoxy, propoxy, isopropoxy or butoxy group. Preferred examples include methoxy and ethoxy groups.

Where substituents $R^1$, $R^2$, $R^3$, $R^5$, $R^6$, $R^7$ or $R^8$ are haloalkoxy groups, said haloalkoxy groups are alkoxy groups as defined above that are substituted with at least one halogen atom and each may be the same or different. Each may be, for example, a trifluoromethoxy, trichloromethoxy, difluoromethoxy, dichloromthoexy, dibromomethoxy, fluoromethoxy, 2,2,2-trichloroethoxy, 2,2,2-trifluoroethoxy, 2-bromoethoxy, 2-chloroethoxy, 2-fluoroethoxy or 2,2-dibromoethoxy group. Preferred examples include trifluoromethoxy, trichloromethoxy and 2,2,2-trifluoroethoxy groups.

Where substituents $R^1$, $R^2$, $R^3$, $R^5$, $R^6$, $R^7$ or $R^8$ are aryloxy groups, said aryloxy groups are aryl groups as defined above that are bonded to an oxygen atom and each may be the same or different. Each may be, for example, a phenoxy, naphthyloxy, phenanthryloxy or anthracenyloxy group.

Where substituents $R^1$, $R^2$, $R^3$, $R^5$, $R^6$, $R^7$ or $R^8$ are alkoxyalkyl groups, said alkoxyalkyl groups are alkyl groups as defined above that are substituted with at least one alkoxy group as defined above and each may be the same or different. Each may be, for example, a methoxymethoxy or 1-methoxyethoxy group.

Where substituents $R^1$, $R^2$, $R^3$, $R^5$, $R^6$, $R^7$ or $R^8$ are alkylcarbonyl groups, said alkylcarbonyl groups are carbonyl groups substituted with a hydrogen atom or an alkyl group as defined above and each may be the same or different. Each may be, for example, a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methyl-pentadecanoyl, 13,13-dimethyltetradecanoyl, heptadecanoyl, 15-methylhexadecanoyl, octadecanoyl, 1-methylheptadecanoyl, nonadecanoyl, eicosanoyl or heneicosanoyl group. Preferred examples include formyl, acetyl, propionyl, pivaloyl and valeryl groups.

Where substituents $R^1$, $R^2$, $R^3$, $R^5$, $R^6$, $R^7$ or $R^8$ are alkoxycarbonyl groups, said alkoxycarbonyl groups are carbonyl groups substituted with an alkoxy group as defined above and each may be the same or different. Each may be, for example, a methoxycarbonyl, ethoxycarbonyl, propoxycarbonyl, butoxycarbonyl, s-butoxycarbonyl, t-butoxycarbonyl or isobutoxycarbonyl group. Preferred examples include methoxycarbonyl and ethoxycarbonyl groups.

Where substituents $R^1$, $R^2$, $R^3$, $R^5$, $R^6$, $R^7$ or $R^8$ are aralkyl groups, said aralkyl groups are alkyl groups as defined above that are substituted by at least one aryl group as defined above and each may be the same or different. Each may be, for example, a benzyl, indenylmethyl, phenanthrylmethyl, anthrylmethyl, α-naphthylmethyl, β-naphthylmethyl, diphenylmethyl, triphenyl-methyl, α-naphthyldiphenylmethyl, 9-anthrylmethyl, piperonyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl or 6-naphthylhexyl group. Preferred examples include benzyl, indenylmethyl and α-naphthylmethyl groups.

Any substituents $R^1$, $R^2$, $R^3$, $R^5$, $R^6$, $R^7$ or $R^8$ may be used as long as they do not interfere with the reaction of the compound of formula (IV) with the compound of formula $R^4$—L. It will be appreciated that certain substituents can be less suitable. In particular, as the reaction is performed in the presence of a base that removes the hydrogen atom α to the substituent $R^1$, it is preferable for the substituents $R^2$, $R^3$, $R^5$, $R^6$, $R^7$ and $R^8$ to be ones that are not capable of forming an anion in the presence of a base, in particular not hydroxyl groups, carboxyl groups or alkylcarbonyl groups. However, it is possible for the reaction according to the invention to be performed with a starting material having a substituent that is capable of forming an anion with a base if multiple equivalents of the base are used to form the anions as well as removing the hydrogen atom α to the substituent $R^1$.

The leaving group L is any group that is capable of undergoing an insertion reaction with palladium. Typical examples of such groups include those disclosed in D A Culkin & J F Hartwig, *Accounts of Chemical Research* (2003), 36(4), 234-245; J F Hartwig et al, *J Am Chem Soc* 2002, 124, 12557-12565; J F Hartwig & D A Culkin, *J Am Chem Soc* 2002, 124, 9330-9331; and W A Moradi & S L Buchwald, *J Am Chem Soc* 2001, 123, 7996-8002. Preferred examples include halogen atoms such as chlorine, bromine and iodine atoms; sulfonates such as $C_{1-6}$ alkylsulfonates (e.g. methylsulfonate) and optionally-substituted arylsulfonates (e.g. p-toluenesulfonate); and compounds comprising carbon-metal bonds such as C—Mg, C—Li and C—Si. Particularly preferred are bromine and iodine.

Where it is desired to form a diarylated or diheteroarylated compound of formula (I) having leaving groups on the rings thereof (e.g. 2,7-dibromo substituted diarylfluorenes), because the reaction of the present invention involves reaction between a deprotonated benzylic carbon atom and a palladium inserted group of formula $R^4$—Pd—L, it is generally preferable to arylate the compound of formula (IV) first and to then react the resulting compound of formula (I) with a suitable derivatising agent to introduce the desired leaving groups at the desired positions (e.g. the bromo groups at the 2- and 7-positions of the diarylfluorene). The absence of leaving groups such as bromine atoms on the starting material of formula (IV) during the palladium coupling step avoids the possibility of an unwanted coupling reaction at the site of substitution of said leaving groups.

However, it is not essential to exclude leaving groups such as halogen atoms from the starting material of formula (IV) because we have discovered that, under certain conditions, it is possible to react selectively at the desired position. Thus, for example, it is possible to brominate fluorene first and then arylate using phenyl iodide, based on the higher reactivity of the aryl iodide, e.g. using the following conditions:

Pd₂dba₃
BPP^tBu₂
NaO^tBu
Toluene, 105° C.

Any solvent may be used, as long as it does not interfere with the reaction of the invention and it dissolves the reactants at least to some extent. As the reaction is performed in the presence of a base, the solvent used should ideally be aprotic (e.g. not an alcohol or water) and be stable in the presence of a base (e.g. not an ester). Preferred aprotic solvents may be polar or non-polar. Examples of particularly preferred solvents include alkylated benzenes such as xylene and toluene and ethers such as diethyl ether, diisopropyl ether, tetrahydrofuran and dioxane. Of these, toluene is particularly preferred.

The base used in the reaction of the invention to remove the hydrogen atom α to the substituent $R^1$ is any that is sufficiently strong to effect said deprotonation. Preferably, the base should be one that is at least partially soluble in the solvent used. This can be an inorganic salt such as potassium carbonate and caesium carbonate in a polar solvent such as THF or dioxane. Preferred bases are ones which have groups that facilitate dissolution in organic solvents, e.g. alkali metal alkoxides such as sodium methoxide, potassium methoxide, sodium ethoxide, potassium ethoxide, sodium t-butoxide and potassium t-butoxide, and tetraalkylammonium hydroxides such as tetramethylammonium hydroxide and tetraethylammonium hydroxide. Of these, potassium ethoxide and potassium t-butoxide are more preferred and potassium t-butoxide is most preferred. The amount of base used will vary depending on the nature of the reactants, and in particular whether the reaction of the invention involves only a monoarylation (and thus a single deprotonation reaction) or a diarylation (and thus two deprotonation reactions). Typically, from 1 to 10 molar equivalents of base compared to the amount of starting compound of formula (IV) are used; more preferably, from 2 to 5 molar equivalents are used and most preferably from 2 to 4 molar equivalents are used.

Compounds of formula (I) wherein m=0 are non-coupled "fluorene-type" compounds.

Compounds of formula (I) wherein m=1, X is a single bond and two groups $R^2$ do not together represent a group of formula (II) and two groups $R^3$ do not together represent a group of formula (III) are fluorene derivatives.

Compounds of formula (I) wherein m=1, X is a single bond and 2 adjacent groups $R^2$ are together a group of formula (II) wherein Y is a single bond are indenofluorene derivatives.

Compounds of formula (I) wherein m=1, X is a O and two groups $R^2$ do not together represent a group of formula (II) and two groups $R^3$ do not together represent a group of formula (III) are xanthene derivatives.

Compounds of formula (I) wherein m=1, X is a S and two groups $R^2$ do not together represent a group of formula (II)

and two groups $R^3$ do not together represent a group of formula (III) are thioxanthene derivatives.

EXAMPLES

The invention may be further understood by reference to the following non-limitative example.

Example 1

Synthesis of 2,7-dibromo-9,9-diphenylfluorene

Step 1: Synthesis of 9,9-diphenylfluorene 1.1 Raw Materials

| Name | Supplier | Fw | ρ [g/ml] | Equiv | Moles | Vol or Mass |
|---|---|---|---|---|---|---|
| Fluorene | Acros | 166.22 | | 1 | 0.60 | 100 g |
| Iodobenzene | Fluka | 204.01 | 1.826 | 2.5 | 1.50 | 168 mL |
| Potassium -tert-butoxide | Aldrich | 112.21 | | 3 | 1.80 | 202.5 g |
| Pd(OAc)₂ | Aldrich | 224.50 | | 1% | 0.006 | 1.35 g |
| Tricyclohexyl phosphine | Strem | 280.43 | | 1% | 0.006 | 1.68 g |
| Toluene | Romil | | | | | 3.5 L |
| Methanol | Romil | | | | | 1 L |

1.2 Apparatus Set-Up

A 5 L 3 necked round bottom flask equipped with an overhead stirrer, reflux condenser, inside thermometer and nitrogen inlet.

1.3 Experimental Procedure

Fluorene (100 g) was dissolved in 3.5 L toluene and the reaction vessel was then flushed with nitrogen.

Iodobenzene (168 mL) was added and the mixture stirred for 10 min.

The ligand tricyclohexylphosphine (1.68 g) and the catalyst Pd(OAc)₂ (1.35 g) were added at the end of this time, followed by potassium tert-butoxide (202.5 g). The reaction mixture turned dark orange/red.

The resulting mixture was then heated (130° C. oil bath temperature). When the internal temperature reached ≈100-105° C. an exotherm was observed and the heat source was removed until the solution stopped refluxing. The mixture was then heated to reflux (130° C. oil bath temperature) overnight.

After cooling down to room temperature, the reaction was quenched by carefully pouring it into 2 L of water and the resulting mixture was stirred for 0.5 hours.

The phases were separated and the aqueous phase was extracted two more times with 500 mL toluene.

The combined organic phases were filtered through a plug of Silica (Ø30 cm, height 100 cm) and eluted with toluene.

The filtrate was evaporated to give a brown-yellow solid, which was triturated in 1 L methanol for ≈3 hours and filtered off. The thus obtained slightly yellowish solid was dried at 40° C. in high vacuum.

174.1 g (90.9%) of the target product 9,9-diphenylfluorene (DPF) were obtained.

1.4 Analytical Specifications

The product was 97.16% pure by HPLC, which is sufficient to be used in the next step.

1.5 Characterization $^1$H-NMR: $^1$H NMR (CDCl₃) δ 7.57 (2H, d, J=7.6); 7.41 (2H, d, J=7.6); 7.36 (2H, dd, J=7.6); 7.27 (2H, dd, J=7.6) 7.17-7.21 (10H, m).

$^{13}$C NMR (CDCl₃) δ151.46, 146.21, 140.44, 128.45, 128.41, 127.95, 127.71, 126.87, 126.49, 120.40, 65.95.

Step 2: Synthesis of 2,7-dibromo-9,9-diphenylfluorene 1.6 Raw Materials

| Name | Supplier | Fw | ρ [g/ml] | Equiv | Moles | Vol or Mass |
|---|---|---|---|---|---|---|
| DPF | | 318.41 | — | 1.0 | 0.1 | 31.5 g |
| Bromine | Aldrich | 159.82 | 3.10 | 4.6 | 0.46 | 24 mL |
| Iodine | Romil | 253.81 | — | 0.5% | 0.0004 | 0.06 g |
| Dichloromethane | Fisher | 84.93 | 1.32 | — | | 800 mL |
| Sodium carbonate | Fisher | 105.99 | — | 0.5 | 0.05 | 5.25 g |
| Deionised Water | In-house | — | — | — | | 500 mL |
| Sodium hydroxide 10% aq | In-house | — | — | — | | 500 mL |

1.7 Apparatus Set-Up

Reaction Vessel:

A 2 L, 3-neck round bottomed flask equipped with an overhead stirrer, pressure equalised dropping funnel and spirit thermometer.

1.8 Experimental Procedure 9,9-diphenylfluorene (31.5 g) from Step 1 was dissolved in dichloromethane (800 mL). To this sodium carbonate solution (5.25 g in 500 mL water) was added and the reaction mixture cooled to between 0-5° C. using an ice bath.

Iodine (0.6 g) was added followed by dropwise addition of bromine (12 mL) via the dropping funnel to the reaction mixture maintaining the temperature below 5° C. (addition time approx. 30 minutes). Once the addition was complete the ice bath was removed and the reaction mixture was left stirring overnight while warming to room temperature.

At the end of this time, the reaction mixture was again cooled and another 12 mL bromine were added to the dropping funnel. Addition to the reaction mixture was carried out maintaining the temperature below 5° C. (addition time approx. 30 minutes). Once the addition was complete the ice bath was removed and the reaction mixture was left stirring overnight while warming to room temperature.

At the end of this time, the reaction mixture was transferred to a separation funnel, the phases were separated, and the aqueous phase was extracted twice with dichloromethane (300 mL). The organic phases were washed with sodium hydroxide (10% aq, 500 mL) and then dried over $MgSO_4$.

Evaporation resulted in a yellowish solid, which was recrystallized twice from acetonitrile (220 mL)/toluene (320 mL).

31.4 g of the title compound 2,7-dibromo-9,9-diphenylfluorene (65%) were obtained as a colourless solid.

1.9 Analytical Specifications

The final product is 99.68% pure by HPLC and can be used for polymer syntheses.

1.10 Characterization $^1$H-NMR (400 MHz): $^1$H NMR ($CDCl_3$) δ 7.59 (2H, d, J=8.0), 7.50 (2H, s), 7.48 (2H, d, J=8.8), 7.25-7.27 (6H, m), 7.14-7.16 (4H, m); $^{13}$C NMR ($CDCl_3$) δ 153.24, 144.67, 138.34, 131.21, 129.69, 128.9, 128.22, 127.43, 122.10, 121.81, 65.91.

The invention claimed is:

1. A process for the synthesis of a compound of formula (I):

(I)

wherein:
m=0 or 1;
n and p are the same or different and each is 0 or an integer from 1 to 4;
X is a single bond, O, S or NH;
$R^1$ is selected from the group consisting of hydrogen atoms, alkyl groups as defined below, alkenyl groups as defined below, alkynyl groups as defined below, aryl groups as defined below and heteroaryl groups as defined below;
$R^4$ is selected from the group consisting of aryl groups as defined below and heteroaryl groups as defined below; and
each $R^2$ and $R^3$ is the same or different and is selected from the group consisting of alkyl groups as defined below, alkenyl groups as defined below, alkynyl groups as defined below, haloalkyl groups as defined below, cyano groups, nitro groups, halogen atoms, hydroxyl groups, carboxy groups, alkoxycarbonyl groups as defined below, alkylcarbonyl groups as defined below, alkoxy groups as defined below, haloalkoxy groups as defined below, alkoxyalkyl groups as defined below, aryl groups as defined below, heteroaryl groups as defined below, aryloxy groups as defined below and aralkyl groups as defined below, or two $R^2$ groups on adjacent carbon atoms together represent a group of formula (II):

(II)

wherein:
q is 0 or an integer from 1 to 4;
Y is a single bond, $CH_2$, O, S or NH;
$R^8$ is selected from the group consisting of alkyl groups as defined below, alkenyl groups as defined below, alkynyl groups as defined below, aryl groups as defined below and heteroaryl groups as defined below; and
each $R^5$ is the same or different and is selected from the group consisting of alkyl groups as defined below, alkenyl groups as defined below, alkynyl groups as defined below, haloalkyl groups as defined below, cyano groups, nitro groups, halogen atoms, hydroxyl groups, carboxy groups, alkoxycarbonyl groups as defined below, alkylcarbonyl groups as defined below, alkoxy groups as defined below, haloalkoxy groups as defined below, alkoxyalkyl groups as defined below, aryl groups as defined below, heteroaryl groups as defined below, aryloxy groups as defined below and aralkyl groups as defined below, and/or two $R^3$ groups on adjacent carbon atoms together represent a group of formula (III):

(III)

wherein:
r is 0 or an integer from 1 to 4;
Z is a single bond, $CH_2$, O, S or NH;
$R^6$ is selected from the group consisting of alkyl groups as defined below, alkenyl groups as defined below, alkynyl groups as defined below, aryl groups as defined below and heteroaryl groups as defined below; and
each $R^7$ is the same or different and is selected from the group consisting of alkyl groups as defined below, alkenyl groups as defined below, alkynyl groups as defined below, haloalkyl groups as defined below, cyano groups, nitro groups, halogen atoms, hydroxyl groups, carboxy groups, alkoxycarbonyl groups as defined below, alkylcarbonyl groups as defined below, alkoxy groups as defined below, haloalkoxy groups as defined below, alkoxyalkyl groups as defined below, aryl groups as defined below, heteroaryl groups as defined below, aryloxy groups as defined below and aralkyl groups as defined below;
said alkyl groups are straight or branched alkyl groups having from 1 to 20 carbon atoms;

said alkenyl groups are straight or branched alkenyl groups having from 2 to 20 carbon atoms;
said alkynyl groups are straight or branched alkynyl groups having from 2 to 20 carbon atoms;
said aryl groups are aromatic hydrocarbon groups having from 6 to 14 carbon atoms in one or more rings which may optionally be substituted with at least one substituent selected from the group consisting of cyano groups, nitro groups, halogen atoms, hydroxyl groups, carboxy groups, alkoxycarbonyl groups as defined below, alkylcarbonyl groups as defined below, amino groups, alkoxy groups as defined below, alkyl groups as defined above, haloalkyl groups as defined below, alkoxyalkyl groups as defined below, aryl groups, aryloxy groups as defined below and aralkyl groups as defined below;
said heteroaryl groups are 5- to 7-membered aromatic heterocyclic groups containing from 1 to 3 heteroatoms selected from the group consisting of sulfur atoms, oxygen atoms and nitrogen atoms, said groups optionally being substituted with at least one substituent selected from the group consisting of cyano groups, nitro groups, halogen atoms, hydroxyl groups, carboxy groups, alkoxycarbonyl groups as defined below, alkylcarbonyl groups as defined below, amino groups, alkoxy groups as defined below, alkyl groups as defined above, haloalkyl groups as defined below, alkoxyalkyl groups as defined below, aryl groups as defined above, aryloxy groups as defined below and aralkyl groups as defined below;
said haloalkyl groups are alkyl groups as defined above which are substituted with at least one halogen atom;
said alkoxy groups are alkyl groups as defined above that are bonded to an oxygen atom;
said haloalkoxy groups are alkoxy groups as defined above that are substituted with at least one halogen atom;
said aryloxy groups are aryl groups as defined above that are bonded to an oxygen atom;
said alkoxyalkyl groups are alkyl groups as defined above that are substituted with at least one alkoxy group as defined above;
said alkylcarbonyl groups are carbonyl groups substituted with a hydrogen atom or an alkyl group as defined above;
said alkoxycarbonyl groups are carbonyl groups substituted with an alkoxy group as defined above; and
said aralkyl groups are alkyl groups as defined above that are substituted by at least one aryl group as defined above;
said process comprising reacting a compound of formula (IV):

wherein $R^1$, $R^2$, $R^3$, X, m, n and p are as defined above, with a compound of formula $R^4$—L, wherein $R^4$ is as defined above and L is a leaving group, in the presence of a palladium catalyst and a base.

2. A process according to claim 1, comprising derivatizing said compound of formula (I), after synthesis according to said process of claim 1, to give a further compound of formula (I).

3. A process according to claim 1, wherein said palladium catalyst is a palladium catalyst suitable for a reaction that involves the substitution of an acidic hydrogen by an aryl carbocation.

4. A process according to claim 1, wherein said palladium catalyst is in the form of Pd(0) or Pd(II).

5. A process according to claim 1, wherein said palladium catalyst is palladium (II) acetate or bis(dibenzenylidenacetone) palladium (0) ($Pd_2dba_3$).

6. A process according to claim 1, wherein said palladium catalyst comprises a phosphine ligand.

7. A process according to claim 6, comprising introducing said phosphine either by:
   (i) mixing said palladium catalyst with a phosphine; or
   (ii) including the phosphine group as a ligand of the palladium complex.

8. A process according to claim 6, comprising introducing said phosphine by mixing said palladium catalyst with a phosphine selected from trialkylphosphines (wherein each alkyl group is the same or different), tricycloalkylphosphines (wherein each cycloalkyl group is the same or different and has from 3 to 7 carbon atoms) and triarylphosphines (wherein each aryl group is the same or different and is an aromatic hydrocarbon group having from 6 to 14 carbon atoms in one or more rings which may optionally be substituted with at least one substituent selected from the group consisting of cyano groups, nitro groups, halogen atoms, hydroxyl groups, carboxy groups, alkoxycarbonyl groups, alkylcarbonyl groups, amino groups optionally substituted by one or two alkyl groups, alkoxy groups, alkyl groups, haloalkyl groups, alkoxyalkyl groups, aryl groups, aryloxy groups and aralkyl groups).

9. A process according to claim 6, comprising introducing said phosphine by mixing said palladium catalyst with a phosphine selected from the group consisting of triphenylphosphine, tri(t-butyl)phosphine, tricyclohexylphosphine, 10. A process according to claim 6, comprising introducing said phosphine as a ligand of said palladium catalyst, said palladium catalyst being selected from $PdCl_2(PPh_3)2$ and tetrakis(triphenylphosphine)palladium (0).

11. A process according to claim 6, wherein said palladium catalyst comprises a mixture of a palladium (0) or palladium (II) catalyst with a phospine selected from the group consisting of tricyclohexylphosphine, triphenylphosphine and tributylphospine, or the phosphine-containing palladium catalyst PdCl$_2$(PPh$_3$)2.

12. A process according to claim 6, wherein said palladium catalyst comprises a mixture of bis(dibenzenylidenacetone) palladium (0) or palladium (II) acetate with tricylcohexylphosphine.

13. A process according to claim 7, wherein the molar ratio of palladium to phosphine compound in said mixture is in the range of from 10:1 to 1:10.

14. A process according to claim 7, wherein the molar ratio of palladium to phosphine compound in said mixture is in the range of from 2:1 to 1:2.

15. A process according to any claim 7, wherein the molar ratio of palladium to phosphine compound in said mixture is 1:1.

16. A process according to claim 1, wherein the number of molar equivalents of palladium catalyst used compared to the amount of starting compound of formula (IV) is from 0.1 to 10%.

17. A process according to claim 1, wherein the number of molar equivalents of palladium catalyst used compared to the amount of starting compound of formula (IV) is from 0.5 to 2%.

18. A process according to claim 1, wherein the number of molar equivalents of palladium catalyst used compared to the amount of starting compound of formula (IV) is from 0.5-1%.

19. A process according to claim 1, wherein the substituent R$^1$ in the compound of formula (IV) is a hydrogen atom and 2 or more molar equivalents of the compound of formula R$^4$—L are used compared to the amount of the compound of formula (IV), to give a compound of formula (Ib) as follows:

20. A process according to claim 1 wherein said substituents R$^1$, R$^2$, R$^3$, R$^5$, R$^6$, R$^7$ or R$^8$ are alkyl groups selected from the group consisting of methyl, ethyl, isopropyl, and t-butyl groups.

21. A process according to claim 1 wherein said substituents R$^1$, R$^2$, R$^3$, R$^5$, R$^6$, R$^7$ or R$^8$ are alkenyl groups selected from the group consisting of vinyl and 2-propenyl groups.

22. A process according to claim 1 wherein said substituents R$^1$, R$^2$, R$^3$, R$^5$, R$^6$, R$^7$ or R$^8$ are alkynyl groups selected from the group consisting of ethynyl and 2-propynyl groups.

23. A process according to claim 1 wherein said substituents R$^1$, R$^2$, R$^3$, R$^5$, R$^6$, R$^7$ or R$^8$ are aryl groups selected from the group consisting of phenyl and naphthyl groups.

24. A process according to claim 1 wherein said substituents R$^1$, R$^2$, R$^3$, R$^5$, R$^6$, R$^7$ or R$^8$ are heteroaryl groups selected from the group consisting of furyl, thienyl, pyrrolyl, and pyridyl groups.

25. A process according to claim 1 wherein said substituents R$^1$, R$^2$, R$^3$, R$^5$, R$^6$, R$^7$ or are haloalkyl groups selected from the group consisting of trifluoromethyl, difluoromethyl, dichloromethyl, 2-fluoroethyl and 2,2,2-trifluoroethyl groups.

26. A process according to claim 1 wherein said substituents R$^1$, R$^2$, R$^3$, R$^5$, R$^6$, R$^7$ or R$^8$ are alkoxy groups selected from the group consisting of methoxy or ethoxy.

27. A process according to claim 1 wherein said substituents R$^1$, R$^2$, R$^3$, R$^5$, R$^6$, R$^7$ or are haloalkoxy groups selected from the group consisting of trifluoromethoxy, trichloromethoxy, and 2,2,2-trifluoroethoxy groups.

28. A process according to claim 1 wherein said substituents R$^1$, R$^2$, R$^3$, R$^5$, R$^6$, R$^7$ or R$^8$ are aryloxy groups selected from the group consisting of phenoxy, naphthyloxy, phenanthryloxy, and anthracenyloxy groups.

29. A process according to claim 1 wherein said substituents R$^1$, R$^2$, R$^3$, R$^5$, R$^6$, R$^7$ or R$^8$ are alkoxyalkyl groups selected from the group consisting of methoxymethoxy and 1-methoxyethoxy groups.

30. A process according to claim 1 wherein said substituents R$^1$, R$^2$, R$^3$, R$^5$, R$^6$, R$^7$ or R$^8$ are alkylcarbonyl groups selected from the group consisting of formyl, acetyl, propionyl, pivaloyl, and valeryl groups.

31. A process according to claim 1 wherein said substituents R$^1$, R$^2$, R$^3$, R$^5$, R$^6$, R$^7$ or R$^8$ are alkoxycarbonyl groups selected from the group consisting of methoxycarbonyl and ethoxycarbonyl groups.

32. A process according to claim 1 wherein said substituents R$^1$, R$^2$, R$^3$, R$^5$, R$^6$, R$^7$ or R$^8$ are aralkyl groups selected from the group consisting of benzyl, indenylmethyl, and α-naphthylmethyl groups.

33. A process according to claim 1, wherein said leaving group L is selected from the group consisting of halogen atoms, C$_{1-6}$ alkylsulfonates, optionally-substituted arylsulfonates, and compounds comprising carbon-metal bonds.

34. A process according to claim 1, wherein said leaving group L is bromine or iodine.

35. A process according to claim 1, wherein said base is selected from the group consisting of inorganic bases, alkali metal alkoxides, and tetraalkylammonium hydroxides.

36. A process according to claim 1, wherein said base is selected from the group consisting of potassium ethoxide and potassium t-butoxide.

* * * * *